(12) United States Patent
Advani et al.

(10) Patent No.: US 6,379,390 B1
(45) Date of Patent: Apr. 30, 2002

(54) STEMLESS HIP PROSTHESIS

(75) Inventors: Suresh G. Advani; Michael H. Santare, both of Newark; Freeman Miller, Wilmington; Makarand Joshi, Newark, all of DE (US)

(73) Assignee: The University of Delaware, Newark, DE (US)

( * ) Notice: Subject to any disclaimer, the term of this patent is extended or adjusted under 35 U.S.C. 154(b) by 19 days.

(21) Appl. No.: 09/598,791

(22) Filed: Jun. 21, 2000

Related U.S. Application Data

(60) Provisional application No. 60/140,437, filed on Jun. 23, 1999.

(51) Int. Cl.$^7$ .................................................. A61F 2/32
(52) U.S. Cl. .................................. 623/23.11; 623/23.14
(58) Field of Search ........................... 623/23.11, 23.12, 623/23.13, 23.14; 606/74, 65, 67

(56) References Cited

U.S. PATENT DOCUMENTS

| | | | | |
|---|---|---|---|---|
| 4,119,091 A | * | 10/1978 | Partridge | 606/74 |
| 5,007,935 A | * | 4/1991 | Vincent et al. | 623/23.14 |
| 5,376,126 A | * | 12/1994 | Lin | 623/23.11 |
| 5,665,088 A | * | 9/1997 | Gil et al. | 606/74 |

* cited by examiner

Primary Examiner—David J. Isabella
(74) Attorney, Agent, or Firm—Connolly Bove Lodge & Hutz LLP

(57) ABSTRACT

A stemless hip prosthesis uses one or more cables which wrap around the prosthesis and the femur to mount the prosthesis in place thereby avoiding the need to provide the prosthesis with a stem located in the medullary canal.

18 Claims, 1 Drawing Sheet

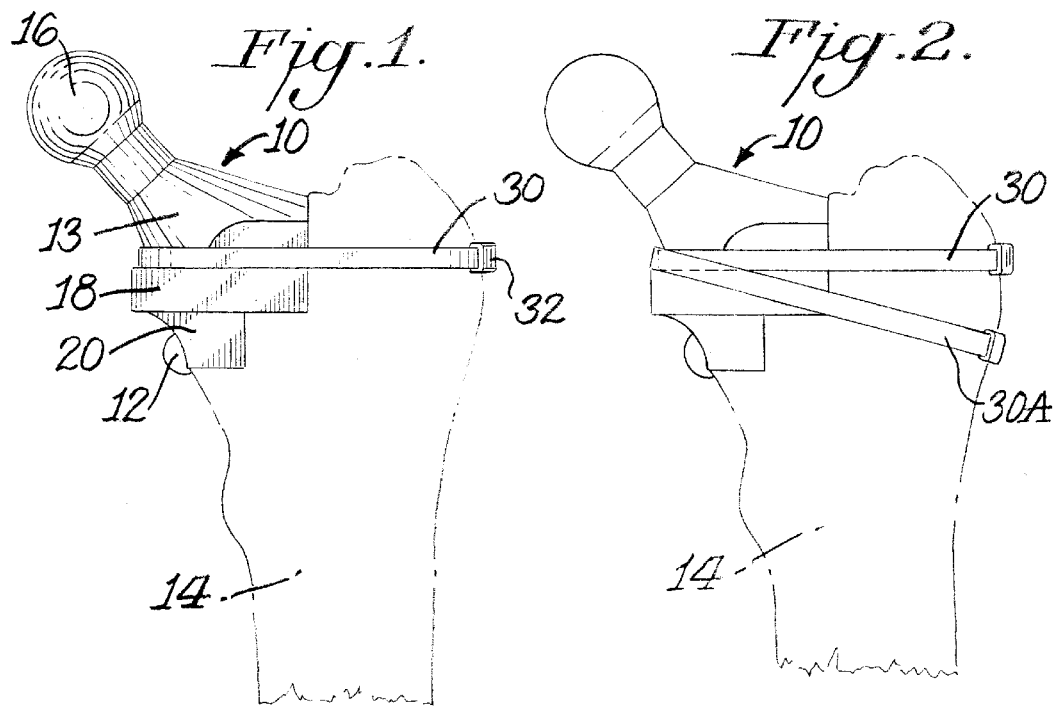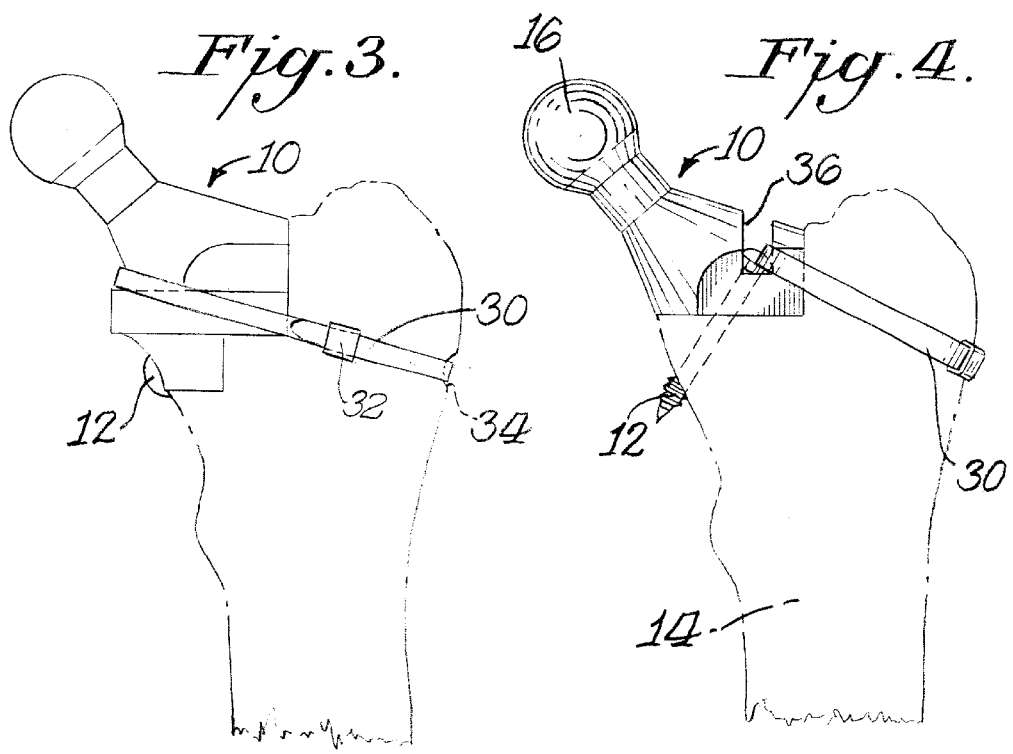

STEMLESS HIP PROSTHESIS

CROSS-REFERENCE TO RELATED APPLICATION

This application is based upon provisional application Ser. No. 60/140,437, filed Jun. 23, 1999.

BACKGROUND OF THE INVENTION

Total hip arthroplasty (THA) using metallic hip prostheses has been successfully performed since the early 1960's and is now a routine procedure. The use of cement to fill the space between the bone and the prosthesis, and bony ingrowth, where the bone grows into a porous prosthesis, have been the two primary methods of fixation used. For the structure of the femur before THA, the load distribution can be essentially resolved into an axial component, two bending moments and a torsional moment which depend upon the leg stance. The distribution of these load components is changed after THA. The current methods of fixation allow for transfer of axial loads to the bone mainly through shear stresses at the bone-implant interface. (The muscles attached to the femur transfer load and moments as before THA.) The bending moment is effectively transferred to the bone, primarily through contact between the prosthesis and bone in two or more localized regions. In addition, the great disparity in the stiffness of a metallic prosthesis and the surrounding bone reduces bending displacements changing the bending moment distribution in the surrounding bone. The current procedure although very successful in the older population has a relatively lower rate of success in the younger population.

A major cause of failure of the prosthesis using the current design methodology is associated with the resorption of the bone which can be the result of stress shielding of the bone caused by the use of a stiff prosthesis as well as the increase in shear stresses at the bone-prosthesis interface. The effective transfer of loads will depend on the stiffness of the prosthesis and the bone-prosthesis interface as well as physiological loading of the proximal end.

The conventional approach for providing a hip prosthesis incorporates the use of a stem mounted in the femur. It would be desirable if a hip prosthesis could be provided which is stemless.

SUMMARY OF THE INVENTION

An object of this invention is to provide a stemless hip prosthesis.

A further object of this invention is to provide such a stemless hip prosthesis which can easily be applied while still maintaining its effectiveness.

In accordance with this invention the prosthesis is mounted to the femur through the use of cables. Preferably the cable or cables are wrapped around a portion of the femur and a portion of the prosthesis.

THE DRAWINGS

FIG. 1 is a side elevational view of a stemless hip prosthesis in accordance with this invention mounted to a femur which is shown in phantom; and FIGS. 2–4 are views similar to FIG. 1 of alternative practices of the invention.

DETAILED DESCRIPTION

The present invention is a new prosthetic device to be used in total hip replacement surgery. It involves a conceptual change from the current design methodology which will enable a long term use of the prosthesis in a relatively younger and active population. The focus of this new approach is to apply the load at the proximal end of the femur rather than transferring the load along the prosthesis stem length. The bending moment is applied across the entire cross section of the femur including the greater trochanter. This approach required the development of a new method of fixation which results in a reduction in interface shear stresses, relative torsion and stress shielding.

The problems identified with the conventional design are as follows: The bending moment is applied through an intermedullary stem resulting in stress concentrations at the proximal, medial and the distal lateral ends of the prosthesis. The axial loads and the torsional moments are transferred to the bone across the bone prosthesis interface resulting in high interface shear stresses. Due to the high stiffness of the prosthesis, there is a reduction in bending displacements, resulting in stress shielding. This disparity in stiffness also contributes to interface shear stresses.

The new design eliminates interface shear stresses by using cables as a means of fixation. Cables support axial loads, but not bending moments. Thus, they do not increase the bending stiffness of the bone. The short flexible stembolt arrangement 12 in the medial calcar region extends through the prosthesis body 13 into the femur 14 and provides torsional support and an anchor while increasing interface shear stresses locally. The bending stiffness of the lateral region is effectively utilized by the later described use of the metal clip-cable arrangement 30. This also provides an anchor and some torsional support. The cables contact the tendon, resulting in only a marginal increase in local stresses. This arrangement allows a more "natural" stress distribution across the proximal femur cross section. Stress shielding is effectively minimized, since there is no increase in the effective bending stiffness of the femur.

An important aspect of this design is the relative ease of revision (if required) which would essentially involve tightening of the cables. In the extreme, revision surgery would be the use of a conventional prosthesis. In this case the new design has a distinct advantage that a very small portion of the bone is initially removed.

The invention could be applied in various manners. In general, a cable 30 which could be in the form of a known surgical high strength steel cable is applied around a portion of the prosthesis 10 and a portion of the femur 14. Such known surgical cable includes a clamping device 32 which would be used to tighten the cable and dispose the cable in its anchored condition. Any excess cable could then be removed. The cable would be sufficiently flexible to conform to the prosthesis and femur around which the cable is wrapped.

FIG. 1 illustrates one practice of the invention wherein the prosthesis 10 includes the generally spherical joint 16 extending from prosthesis body 13 and includes a mounting plate 18 with its downward extension 20. Extension 20 would be located within the bone. A conventional fixation screw 12 would pass through prosthesis 10 into femur 14 at an angle in the known manner. The cable 30 is illustrated as being wrapped around the prosthesis body 13 directly above the plate 18 and around the femur. The cable is then sufficiently tightened by any suitable clamp device 32 to firmly anchor the prosthesis 10 on the femur 14. Such clamp device could be the type of device generally used with surgical high strength cables.

FIG. 2 illustrates a variation wherein either a plurality of cables 30, 30A are wrapped around the prosthesis 10 and the femur 14 or a single cable is wound a multiple number of times around the prosthesis 10 and the femur 14.

FIG. 3 shows a variation wherein a medial lateral hole 34 is drilled in the femur at the angle of cable 30. The cable 30 is threaded through the hole 34 and then wrapped around the femur and prosthesis.

FIG. 4 shows a variation of the invention in which a channel or slot 36 is formed in prosthesis 10 and the cable 30 is located in the channel 36 as well as being wrapped around the femur 14.

As shown in FIG. 4 the slot 36 thus creates a shoulder against which the cable would be located to hold the cable in place. Similarly, as shown in FIG. 1 the mounting plate 18 extends outwardly beyond the peripheral surface of the prosthetic device body. The cable 30 is located against the shoulder so that the shoulder holds the cable 30 in place.

It is thus to be understood that the cables are used in combination with a fixture screw to firmly and effectively anchor the prosthesis in place without the need for a stem extending downwardly from the prosthesis into the medullary canal. The number and location of the cables may vary provided that the cables are wrapped around both the prosthesis and the femur to firmly anchor the prosthesis in place.

What is claimed is:

1. A stemless hip prosthesis comprising a prosthesis body having a joint portion, said body being shaped to fit against the proximal portion of the femur, said body having a peripheral surface, an exposed shoulder at said peripheral surface, a flexible cable disposed against said shoulder to hold said cable in place for being wrapped around said prosthesis and the femur for facilitating the mounting of said prosthesis to the femur, and tightening structure on said cable to tighten said cable around the femur without requiring any separate femur contacting cable holding structure remote from said shoulder.

2. The prosthesis of claim 1 wherein said prosthesis body includes an exposed slot, said exposed slot forming said shoulder, and said cable being disposed in said slot.

3. The prosthesis of claim 2 wherein said tightening structure is a clamp device for tightening said cable.

4. The prosthesis of claim 3 wherein said cable has multiple wraps around said prosthesis body and the femur.

5. The prosthesis of claim 3 wherein a plurality of cables are provided for being wrapped around said prosthesis and the femur.

6. The prosthesis of claim 1 wherein said tightening structure is a clamp device for tightening said cable.

7. The prosthesis of claim 1 wherein said cable has multiple wraps around said prosthesis body and the femur.

8. The prosthesis of claim 1 wherein a plurality of cables are provided for being wrapped around said prosthesis and the femur.

9. In a method of mounting a hip prosthesis in hip replacement wherein a prosthetic device is mounted to the proximal end of a femur, the improvement being in that the prosthetic device is mounted to the femur by disposing a flexible cable against an exposed shoulder on the peripheral surface of the body of the prosthetic device, wrapping a flexible cable around the prosthetic device and the femur while the cable is against the shoulder to anchor the prosthetic device to the femur without inserting a stem into the medullary canal of the femur, and tightening the cable against the femur to hold the cable against the femur with requiring any separate femur contacting cable holding structure remote from the shoulder.

10. The method of claim 9 including drilling at least one hole through the femur, and the threading the cable through the hole.

11. The method of claim 10 including providing a slot in the body of the prosthetic device with the slot thereby forming the shoulder, and disposing the cable in the slot.

12. The method of claim 10 including providing multiple wraps around the prosthetic device and the femur.

13. The method of claim 9 including providing a slot in the body of the prosthetic device with the slot thereby forming the shoulder, and disposing the cable in the slot.

14. The method of claim 9 including providing multiple wraps around the prosthetic device and the femur.

15. The method of claim 9 including wrapping the cable around the femur with the cable in direct contact with the femur at all locations of the cable except where the cable contacts the prosthetic device.

16. The method of claim 9 including providing the prosthetic device with a mounting plate which extends outwardly of the peripheral surface to form the shoulder.

17. The prosthesis of claim 1 including a mounting plate extending outwardly of said peripheral surface to comprise said shoulder.

18. The prosthesis of claim 2 including a passage in said body extending from said slot for a stem-bolt arrangement.

* * * * *